United States Patent [19]

Sanderson et al.

[11] 4,436,927
[45] Mar. 13, 1984

[54] ALKANE ACETATES PRODUCED BY OXIDATIVE ESTERIFICATION OF OLEFINS OVER THALLIUM BORATE

[75] Inventors: John R. Sanderson; Lewis W. Watts, Jr., both of Austin, Tex.

[73] Assignee: Texaco Inc., White Plains, N.Y.

[21] Appl. No.: 402,665

[22] Filed: Jul. 28, 1982

[51] Int. Cl.³ .............................................. C07C 67/05
[52] U.S. Cl. ................................................... 560/246
[58] Field of Search ............... 560/246, 247, 241, 243, 560/244, 245

[56] References Cited

U.S. PATENT DOCUMENTS 4,220,800  9/1980  Stapp ................................... 560/246

*Primary Examiner*—Michael L. Shippen
*Attorney, Agent, or Firm*—Robert A. Kulason; Jack H. Park; Kenneth R. Priem

[57] ABSTRACT

A process for the production of alkane acetates from olefins in the presence of a thallium borate catalyst, oxygen and a carboxylate ion source via oxidative esterification is described. The reaction is conducted at a temperature in the range of 120° to 220° C. and a pressure of 1 atmosphere or greater. Alkane diacetates and hydroxy acetates are produced which may be used as precursors to alkylene oxides, alkylene glycols and other useful compounds.

6 Claims, No Drawings

ALKANE ACETATES PRODUCED BY OXIDATIVE ESTERIFICATION OF OLEFINS OVER THALLIUM BORATE

CROSS-REFERENCES TO RELATED APPLICATIONS

This application is related to U.S. patent applications Ser. No. 402,664, and Ser. No. 402,663, which relate to methods for producing alkane acetates by oxidative esterification of olefins over transition metal borate catalysts. Alkali metal borates are the catalysts in U.S. patent application Ser. No. 402,668, and alkali earth metal borates are the catalysts in U.S. patent application Ser. No. 402,667, for similar oxidative esterification reactions. All of these patent applications are filed of even date.

BACKGROUND OF THE INVENTION

1. Field of the Invention

The invention is related to a process for the production of alkane acetates by the oxidative esterification of olefins, and is particularly related to such a process conducted in the presence of a carboxylate ion source and a thallium borate catalyst.

2. Description of Relevant Methods

The production of ethylene oxide from ethylene has long been known. However, there has been a less successful search for a similar process for producing propylene oxide directly from propylene in an economic manner. The same processes which produced ethylene oxide cannot be adapted to the production of propylene oxide.

As a result, a number of different schemes to produce propylene oxide from propylene or to produce an intermediate to propylene oxide from propylene have been proposed. Initially the research effort seemed to be directed to producing an olefin oxide directly from the olefin in the presence or absence of a solvent. U.S. Pat. No. 2,649,463 describes the production of a coordination complex created by the reaction of an olefin with a metal halide where the metal is copper, platinum, palladium, iridium, aluminum, zinc, silver, mercury or antimony. This coordination complex is further reacted with oxygen at a high temperature to produce the olefin oxide plus oxygen-containing metal halides. Hawkins, et al. in an article entitled, "Autoxidation of Olefins," in the *Journal of Applied Chemistry*, Vol. 6, 1956, pgs 1 through 10, describes a process for the production of epoxides directly from olefins and molecular oxygen over magnesium oxide and/or cobalt naphthenate. The direct production of olefin oxides from a mono olefin and a saturated hydrocarbon with oxygen and water, organic acids or olefin oxide in low concentration is described in U.S. Pat. No. 2,780,634.

British Pat. No. 1,582,261 describes how propylene may be reacted with oxygen over a dinitrogen tetraoxide catalyst in a liquid medium of a chlorinated organic solvent to produce propylene oxide directly. Propylene oxide may also be prepared directly from propylene and oxygen over a catalyst system comprising a palladium cation plus a chloride anion in the presence of a phosphorous or arsenic ligand as revealed in U.S. Pat. No.,4,256,649.

Further, U.S. Pat. No. 2,784,202 outlines how propylene in a liquid hydrocarbon solvent, such as benzene, in the presence of oxygen and water, organic acids or propylene oxide in low concentration yield propylene oxide when heated at a temperature between 130° and 300° C. Propylene oxide is also proposed to be made directly from propylene in benzene in the presence of oxygen over a cobalt, copper, magnesium, vanadium or chromium catalyst where barium or lead is used as a promoter for the catalyst, according to U.S. Pat. No. 3,071,601. Brill, et al. in *Journal of Organic Chemistry*, Vol. 29, 1964, pgs 140–143, describes a process for passing olefins and oxygen, frequently in contact with or dissolved in benzene over various catalysts such as azobisisobutyronitrile, cadmium oxide, cobaltic acetylacetonate, magnesium oxide or methyl ethyl ketone peroxide to produce various oxidation products, including the desired epoxides. U.S. Pat. No. 3,132,156 reveals that ethylene, propylene or butylene oxide may be produced directly from ethane, propane or butane under very precise conditions. These conditions include a temperature of between 425° to 575° C., an oxygen volume percent of between 4 and 14, a contact time with the oxygen of between 0.07–1.5 seconds, a pressure of between 20 to 150 psig and constant concentrations of reactants. Epoxides may also be produced from olefins and oxygen which are in an inert reaction medium when they are brought in contact with a rhenium catalyst and 0.05 to 15 weight percent of a reaction modifier comprised of an alkyl aryl or cyclo alkyl cyanide, pyridine or quinoline in accordance with the invention described in U.S. Pat. No. 3,316,279.

Other schemes for producing olefin oxides from olefins and oxygen by means of a solvent or liquid reaction medium include the following. U.S. Pat. No. 3,153,058 employs polyacyl esters of polyhydroxy alkanes, polyhydroxy cycloalkanes, polyglycols or mixtures thereof as the solvent. Materials selected from saturated aliphatic, alicyclic and aromatic nitriles and mixtures thereof form the solvent in U.S. Pat. No. 3,210,380. Boric acid esters form the liquid reaction medium in U.S. Pat. No. 3,210,381. U.S. Pat. No. 3,228,967 uses major amounts of acetone as the solvent. Carbonic acid esters are employed in U.S. Pat. No. 3,228,968, and at least 25 percent by weight of certain ketones serves as the reaction medium in U.S. Pat. No. 3,232,957. Halogenated benzenes serve as the solvent in U.S. Pat. No. 3,238,229 while benzoic acid esters are employed in a similar reaction described in U.S. Pat. No. 3,281,433. Olefin oxides may be prepared directly from olefins and oxygen over a hydrocarbon soluble, phosphorous molybdenum-hydroxy compound catalyst according to the disclosure in U.S. Pat. No. 3,856,826. The approach of making epoxides directly has never been commercially feasible because all of the methods explored gave low yields of epoxides.

At this point in the history of this research, the emphasis seems to shift from making the olefin oxides directly to making an intermediate which could be converted to the olefin oxides by a second step. For example, U.S. Pat. No. 2,497,408 suggests the production of propylene glycol diacetate from propylene, oxygen and acetic acid over a metal acetate catalyst in which the metal is lead or iron in combination with an alkali earth metal acetate. Another example of this latter approach is U.S. Pat. No. 3,403,175 where olefins in oxygen are reacted in the presence of a reaction medium consisting of carboxylic acid and anhydrides with no catalyst to produce glycol diesters. Acyloxy compounds, which are intermediates to olefin epoxides, may be produced by the reaction of olefins with the metal salt of a carboxylic acid in an aqueous solution if electric current is passed through the solution, according to the method of U.S. Pat. No. 3,453,189. U.S. Pat. No. 3,479,395 reveals that olefins in oxygen may be converted to glycols and glycol acetates by being brought into contact with a solution comprising tellurium dioxide, an alkali metal halide and a redox agent dissolved in a solvent of certain specifications (water, acetic acid, dioxane, dialkyl formamides or dialkyl sulfoxides).

Further examples of the approach to making intermediates to the epoxides include U.S. Pat. No. 3,542,857 where vicinal glycol monoesters and diesters may be made by passing olefins in oxygen in an alkanoic acid medium over cerium salts. A method for making glycol esters from olefins and oxygen in a carboxylic acid medium over tellurium and an appropriate form of bromine is revealed in U.S. Pat. No. 3,668,239. British Pat. No. 1,278,353 teaches that nonvicinal glycols may be reacted with carbon monoxide over a rhodium or iridium catalyst together with a halogen promoter to produce dicarboxylic acids which are precursors to diesters which are intermediates to the epoxides. Further, British Pat. No. 1,326,219 discloses that glycol esters may be produced from olefins and oxygen in the presence of at least one carboxylic acid when a halogen is employed as an anion and a metal cation is present which is selected from the group of tellurium, cerium, antimony, manganese, arsenic or cobalt. Other examples which reveal how esters may be made from olefins include U.S. Pat. No. 3,770,813 where an olefin with a chloro, hydroxy or lower alkanoyloxy substituent together with oxygen and a monobasic carboxylic acid may be reacted together over an iodide anion and a heavy metal cation of atomic numbers 21 to 30 and 48, and nitrogen-containing cations to give glycol esters. Olefins and oxygen may be reacted together over a catalyst system comprising a metal cation of tellurium, cerium, antimony, vanadium, gallium, arsenic, copper, selenium or silver with a bromine or chlorine anion to produce vicinal glycol esters which are later fractionated to give a residue with a boiling point higher than the vicinal glycol esters according to the disclosure in U.S. Pat. No. 3,789,065. The residue is then contacted with a carboxylic acid to yield additional vicinal glycol esters. British Pat. No. 1,353,814 describes the reaction of olefins and oxygen in a carboxylic acid in the liquid phase that contains at least 0.5 percent water over a catalyst system identical to that of the patent previously described to also yield vicinal glycol esters. Ethylene or propylene may be reacted with oxygen in a carboxylic acid over a catalyst system comprising a tellurium cation and a bromide anion or a selenium cation plus a chloride or bromide anion to produce vicinal glycol esters as revealed in U S. Pat. No. 3,907,874.

Aliphatic hydrocarbon carboxylic acid esters of vicinal glycols which contain organic halogen impurities may be purified by passing them over aquobasic alkali metal compounds, aquobasic earth metal compounds or compounds (other than halides) of zinc, lead, cadmium, tin, mercury, silver, manganese, copper, nickel, cobalt, iron or chromium in accordance with the invention in British Pat. No. 1,410,834. German Auslegeschrift No. 2,430,022 describes a multi-step procedure for producing butane diols, which are precursors to butane oxide, from propylene, oxygen and acetic acid.

A system which has obtained a fair amount of commercial importance is described in U.S. Pat. No. 4,045,477 by which vicinal hydroxy esters and diesters are produced from olefins and oxygen over tellurium and an iodide source. Organic monoesters of vicinal glycols may also be produced from olefins, oxygen, water and a carboxylic acid over a system comprising an iodine compound (such as copper iodide, manganese iodide or cerium iodide), a copper compound, and an activated ion taken from the group of manganese, cerium, alkali metals, alkali earth metals, nitric compounds or mixtures thereof, according to the invention in U.S. Pat. No. 4,061,868. U.S. Pat. No. 4,069,381 reveals how glycol monoesters may be made from olefins, oxygen and carboxylic acids over a catalyst system where the cation is zirconium, niobium, molybdenum, hafnium, tantalum, tungsten or rhenium where the anion is a halide in the presence of lithium, sodium, potassium, titanium, vanadium, chromium, manganese, iron, cobalt, nickel, copper, zinc, aluminum or silver.

Some of the more recent patents in this field include the following. Esters may be produced from olefins in an acid plus oxygen over a tin or cerium catalyst in the presence of iodide as revealed by U.S. Pat. No. 4,154,957. Saturated vicinal esters may be produced from olefins, carboxylic acids and oxygen in the presence of a boron-containing catalyst according to the invention of U.S. Pat. No. 4,220,800. U.S. Pat. No. 4,221,916 teaches that olefins, carboxylic acids and oxygen when reacted together over a vanadium or ruthenium-containing catalyst can also produce saturated vicinal esters. U.S. Pat. No. 4,238,624 discloses a procedure by which ethylene, oxygen and a lower alkanoic acid are reacted together over an iodine source in a bismuth stabilized tellurium oxide catalyst on a carbon support to give ethylene glycol mono-and dialkanoates.

Further, alkylene glycol dicarboxalates may be made from carboxylic acid esters of monohydric or polyhydric short chain alcohols and olefins and oxygen over a catalyst system comprising tellurium, cerium, antimony, manganese, vanadium, gallium, arsenic or cobalt, plus a halogen anion and a hydrolyzing agent in addition to water as taught by U.S. Pat. No. 4,239,911.

Methods also exist for converting the ester intermediates into the epoxides. For example, U.S. Pat. No. 4,012,423 describes how vicinal hydroxy esters may be reacted over group I, II and IIIA basic metal carboxylates, being the preferred catalyst (sodium, potassium, lithium, calcium or barium, etc.), or group I, II and IIIA basic metal simple oxides and complex oxides and organic bases (such as borates, phosphates, oxides and carboxylates, particularly sodium borate, nickel oxide, etc.) to give epoxides. Another method is described in U.S. Pat. No. 4,158,008 whereby propylene glycol monoesters in the presence of a high boiling solvent is reacted over a base to produce propylene oxide. Propylene oxide may also be produced from propylene glycol with the removal of a water molecule over a weakly acidic carrier comprising a basic alkali metal salt of a low molecular weight carboxylic acid as taught by U.S. Pat. No. 4,226,780.

Of the numerous patents discussed so far, the ones considered to be most relevant to the invention at issue are U.S. Pat. Nos. 4,012,423; 4,069,381 and 4,220,800, all of which have been discussed.

Despite all of the investigative routes described so far and the ones that have been devised which have not been described, there is still a need for an efficient method for making propylene oxide from propylene, in addition to making the alkylene oxides from other olefins, which does not involve a highly corrosive or highly expensive catalyst system.

SUMMARY OF THE INVENTION

The invention concerns a process for the production of alkane acetates comprising reacting an olefin or a mixture of olefins with oxygen and a carboxylate ion source, in the presence of a thallium borate catalyst.

DETAILED DESCRIPTION OF THE PREFERRED EMBODIMENTS

Alkane hydroxy acetates and diacetates, also called glycol monoesters or diesters or vicinal diesters, may be prepared by the oxygen or air oxidation of olefins in a carboxylic acid and/or anhydride solvent in the presence of a transition metal borate catalyst. The diacetates may be converted to epoxides or glycols using methods known in the art, some of which have been outlined previously. Both the epoxides and the glycols are of interest in the manufacture of important high volume products, including urethane polyols, gasoline additives, and heat transfer fluids.

According to the method of this invention, the olefin feedstocks may consist of any mono olefin having the double bond located anywhere within the molecule and mixtures of such olefins. The olefin may be an alpha or an internal olefin. Specific examples of suitable feedstocks include, but are not limited by, the following list: propylene, 1-butene, 2-butene, 1-pentene, 2-pentene, 1-hexene, 2-hexene, 3-hexene, heptenes, octenes, nonenes, decenes, undecenes, dodecenes, tridecenes such as 6-tridecene, tetradecenes such as 7-tetradecene, pentadecenes, hexadecenes, etc., and mixtures thereof. Preferably, the olefin has 3 to 16 carbon atoms.

Of course, molecular oxygen in a pure form or air is an essential co-reactant for the method of this invention.

The co-reactant and solvent must be a compound capable of generating a carboxylate ion when it serves as a solvent. These compounds may be generally described as carboxylic acids or anhydrides. They may include materials such as acetic acid, acetic anhydride, carboxylic acids, although acetic acid is the especially preferred solvent/co-reactant.

Catalysts found to be useful in the method of this invention include metal borates. Borate compounds are novel for the catalysis of olefins to olefin acetates and diacetates (also called esters and diesters) never having been previously discovered. The especially preferred borate is thallium borate. These catalysts are much less corrosive than many of those used in other methods, especially the halide systems. Also, much smaller catalyst levels may be used. They are also less expensive than many of the catalyst systems proposed.

The reaction conditions under which the method of this invention may be conducted include a temperature range of from 80° to 280° C. A preferred range is from 120° to 220° C. The pressure may be one atmosphere or higher. These conditions are much milder than many of those in the prior art discussed earlier.

The invention will be further illustrated by the following examples which are not intended to limit the scope of the invention except as noted.

EXAMPLES 1–4

A one-liter glass-lined autoclave equipped with a magnetic stirrer was charged with 300 ml acetic acid and 1 g thallium borate. The autoclave was sealed and 42 g of propylene pressured in. The autoclave was heated to 150° C. The autogeneous pressure was 540 psig. The mixture was pressured slowly to 600 psig with oxygen and held at 600 psig (by repressuring with oxygen from time to time) for four hours. The reactor was then cooled and vented. Vapor phase chromatography results are shown in Table I along with additional examples.

TABLE I

| | OXIDATIVE ESTERIFICATION CATALYZED BY THALLIUM BORATE | | | | |
|---|---|---|---|---|---|
| Example | Thallium Borate (g) | Temp., (°C.) | Time, (Hr) | Mono-acetate (g) | Di-acetate (g) |
| 1 | 1.0 | 150 | 4 | 4.0 | 8.6 |
| 2 | 1.0 | 160 | 2 | 7.7 | 8.3 |
| 3 | 1.0 | 160 | 4 | 3.6 | 13.7 |
| 4 | 1.5 | 150 | 2 | 1.9 | 1.4 |

Many modifications may be made in the method of this invention by those skilled in the art to maximize the yields of the desirable acetates without departing from the spirit and scope of the invention which is defined only by the appended claims. For example, one skilled in the art could determine an exact combination of thallium borate catalyst amounts, temperatures, feedstocks and modes of addition to optimize the yield.

We claim:

1. An improved process for the production of alkane hydroxy acetates and diacetates by reacting an olefin or a mixture of olefins with oxygen and a carboxylate ion source selected from the group consisting of acetic acid and acetic anhydride, wherein the improvement comprises conducting the reaction in the presence of thallium borate.

2. The process of claim 1 in which the reaction is conducted at a temperature in the range of 120° to 220° C.

3. The process of claim 1 in which the olefins have 3 to 16 carbon atoms.

4. The process of claim 1 in which the olefin is propylene.

5. An improved process for the production of alkane hydroxy acetates and diacetates by reacting an olefin or a mixture of olefins where each molecule has 3 to 16 carbon atoms, with oxygen in the presence of acetic acid at a temperature in the range of 120° to 220° C., wherein the improvement comprises conducting the reaction in the presence of thallium borate.

6. The process of claim 5 in which the olefin is propylene.

* * * * *